United States Patent [19]
Cole

[11] Patent Number: 5,392,114
[45] Date of Patent: Feb. 21, 1995

[54] FLUID POLLUTION MONITOR

[76] Inventor: Martin T. Cole, 7 Loxwood Avenue, Keysborough, Vic., 3173, Australia

[21] Appl. No.: 884,398

[22] Filed: May 18, 1992

Related U.S. Application Data

[63] Continuation-in-part of Ser. No. 842,452, Feb. 27, 1992, abandoned, which is a continuation of Ser. No. 585,099, Sep. 28, 1990, abandoned.

[30] Foreign Application Priority Data

Mar. 30, 1988 [AU] Australia .................. PI7512

[51] Int. Cl.⁶ .................... G01N 21/53; G08B 17/107
[52] U.S. Cl. ............................ 356/338; 250/574; 340/630; 356/341
[58] Field of Search .............. 356/338, 341, 446; 250/574; 340/630

[56] References Cited

U.S. PATENT DOCUMENTS 3,515,482  6/1970  Garrow et al. .
3,756,720  9/1973  Skala .................. 356/37

FOREIGN PATENT DOCUMENTS 8909392 10/1992 WIPO .

*Primary Examiner*—Jill A. Warden
*Attorney, Agent, or Firm*—Learman & McCulloch

[57] ABSTRACT

A pollution monitoring device including a fluid sampling chamber (21), a collimated light source (14, 15) directing a light beam (10, 11) into the chamber, a port (23) for introducing sample fluid into the chamber exposed to the light beam, a light detector cell (16) separated or shaded from the light beam and focussing apparatus (17) for directing scattered light produced by the presence of suspended particles and molecules in the chamber towards the detector. The source may be two lasers with co-linear beams or an LED. There is also disclosed a sample area of small diameter in which a light beam traverses the area across the flow path of a sample fluid and a projector projecting scattered light from particles into a light receiving zone of notional triangular shape having an included angle of less than 60°, to enable discrimination of particle size discrimination.

12 Claims, 4 Drawing Sheets

FLUID POLLUTION MONITOR

This application is a continuation-in-part of application Ser. No. 07/842,452, filed Feb. 27, 1992, now abandoned, which was a continuation of application Ser. No. 07/585,099, filed Sep. 28, 1990, now abandoned.

BACKGROUND OF THE INVENTION

The present invention relates to detection and monitoring equipment for fluid pollution, including smoke and air pollution by light scatter techniques.

Devices are known for the detection of smoke by light scatter techniques. Such devices include a light source configured to irradiate through a volume of air provided in a sampling region in which smoke, dust or like particles may be suspended. Light scattered off said particles is collected on a light detector means. The amplitude of the signal from said light detector is an indication of the quantity of particulates in the fluid.

Particularly sensitive versions of such detectors are capable of monitoring low levels of fluid pollution and thus may be a useful tool for monitoring general atmospheric pollution. Such high sensitivity enables detection of fires at the earliest possible (incipient) stage, whereby the fire may be controlled by local personnel using portable extinguishers or by removal of the source of heat (e.g. by disconnection of electric current) before smoke levels become dangerous to life. Such detectors require a sensitivity as high as twenty micrograms of wood smoke per cubic meter for example, which is equivalent to a visual range of 40 kilometers.

The monitors disclosed in my earlier Australian Patent Specification Nos. 31843/84, 31842/84, 34537/84, 31841/84 and 42298/85 were developed primarily to detect the very earliest traces of smoke from overheating substances before fire develops. This has nowadays become a critical requirement because of the widespread use of synthetic materials in furniture and furnishings, wiring and equipment. Synthetic materials burn more fiercely and produce toxic fumes at rates considerably higher than their outmoded natural counterparts. Very early detection of smouldering has become vital to the preservation of life (e.g. dormitories) and valuable equipment (e.g. computers).

This prior apparatus can and does summon human intervention before smoke levels become dangerous to life or delicate equipment, it can cause an orderly shutdown of power supplies so that equipment overheating will subside (thereby preventing a fire), or it can operate automatic fire suppression and personnel evacuation systems.

The prior art utilizes a sampling chamber as described in Australian Specification No. 31843/84 through which a representative sample of air within the zone to be monitored, is continuously drawn by an aspirator. The air sample is normally irradiated by an intense, wideband light pulse from a Xenon lamp. A minuscule proportion of the incident photons are scattered off airborne particles towards a very sensitive detector, to produce an analog signal which, after signal processing, represents the level of pollution (smoke) present in the air. The instrument is so sensitive that photons scattered off air molecules alone are detected. Therefore, minor pollution is readily detected as an increased signal. Despite the greater sensitivity of the known apparatus the rate of false alarms is much lower than for conventional smoke detectors (which are comparatively insensitive, by two or three orders of magnitude).

British Specification No. 2045456 (Kallander) discloses a device for detecting the presence of suspended particles in a gas wherein a collimated light beam is directed through a measuring chamber, the chamber including an internally reflecting elliptical cylindrical reflector, the light beam coinciding with one focal axis and a light detector being arranged on the other focal axis. A radiation trap for the unscattered light beam is also disclosed.

Japanese Specification no. 6093944 (Okuda) discloses a detector not having a lens in which laser beam light crosses a small diameter specimen stream at right angles to a first parabolic surface mirror with a photoelectric converter (detector) provided at the focus of a second parabolic surface mirror.

The Okuda reference provides for a double reflection of the scattered light, thereby requiring careful optical alignment but leading to difficulty in achieving optical gain and maintaining alignment in use, particularly where the device is destined for use in vibrating and temperature variable environments.

Furthermore, Okuda is silent in respect of the cone angle within which scattered light emanates from the specimen stream and reflected onto to the detector cell.

U.S. Pat. No. 4,426,640 (Becconsall) discloses a pollution monitoring device using two laser beams of different wave lengths.

Japanese Specification no. 57.69230 (Mino) discloses a smoke detector in which light beams are transmitted to a smoke chamber through optical fibres.

OBJECTIVES OF THE INVENTION

Photons scattered off air molecules are invisible to the naked eye, like faint starlight, whereas in the case of a xenon lamp or a tightly focussed laser beam the incident light is of similar brilliance to sunlight (thus in the one instrument, the range of light levels spans "cosmic proportions"). The task is to detect the equivalent of faint starlight in the presence of sunlight. This requires a chamber of advanced optical design, to separate the desired scattered light from the incident light, and advanced electronics to detect the minuscule scattered light component without resort to cryogenics or photomultipliers.

The prior art has utilized a Xenon lamp as a suitable source of intense wideband light with low energy input. However, in view of the reducing cost of current laser technology it is the object of this invention to utilize the properties of coherent collimated light to simplify the design of the said sampling chamber, to improve the stability of sensitivity, and to reduce the power consumption for the whole instrument.

Furthermore it is an object of the present invention to provide a sampling chamber and detector requiring a small size air passage through which a laser beam is projected.

Said laser beam is projected through a first aperture to traverse the air passage and impinge upon foreign particles that may be entrained in the passage such that scattered light rays are confined by a second aperture to form a well defined conical zone having its apex in the centre of the air passage. A further objective of the invention is to utilize a single reflection of impinging scattered light rays minimizing loss of sensitivity whilst providing optical gain in the system.

It is a further objective of the invention to provide a pollution detector capable of discriminating between the detection of particles in different size ranges. For example smoke particles fall within the range of 0.1 to 25 microns, whereas dust particles are usually larger. Therefore it is a specific objective of the invention to provide a detector which is capable of classifying detected particles according to their size.

SUMMARY OF THE INVENTION

There is provided according to the present invention a fluid pollution monitoring apparatus including a fluid sampling means, means for projecting a coherent collimated light beam into said sampling means, means introducing sample air from an area to be monitored into said sample means to be exposed to said light beam, a light detector cell positioned at a location separated or shaded from the axis of said light beam, and means for directing any scattered light produced by the presence of airborne particles in the sample means towards said detector, said directing means being adapted to focus said scattered light onto said detector cell, the scattered light pattern being of cone shape in cross-section taken on a plane along the axis of said coherent collimated light beam such that said scattered light receiving zone is formed by a conical area having an included angle not exceeding 50°.

The advantage of a coherent collimated light source is that light is not visible beyond the axis of the light beam, except as a result of light scattering off airborne particles. Furthermore it has been found that limiting the cone angle of received scattered light to 50° or less will minimise loss of sensitivity in the detection apparatus.

In a further aspect of the invention, the cross-sectional diameter of the sample means exposed to said light beam is maintained at less than 6 mm, which is large enough to minimise pressure drop in the aspiration apparatus while minimizing the area of the monitored stream to match the small size of said light beam.

If a light beam is projected through the sampling means and does not impinge on any particles, its beam is invisible to the off-axis light detector cell. The introduction of airborne particles which scatter the light beam, produce light capable of detection by said off-axis light detector cell. The incident light beam can be projected or reflected out through and beyond said receiving zone, such that it is conveniently absorbed outside the receiving zone and thereby readily separated from scattered light within said receiving zone. Thus the detector cell positioned within the receiving zone is responsive only to the scattered light component.

Output from said detector cell varies in proportion to the level of scattered light, providing a measure of the concentration of particles within said sampling means.

Whereas light may be predominantly scattered omni-directionally for gas molecules, in the case of larger particles, such as smoke, the majority of scattering occurs within 0° to 30° off the axis of said light beam. Accordingly, however it is an important aspect of this invention that the included angle of the scattered light receiving zone is maintained at 25° or less relative to the axis of said light beam and to achieve this requires optical gain.

In a preferred form of the invention it is proposed to enhance the capture of light scattered in the forward direction (that is, at small angles to the axis of the laser beam). This approach would provide greater sensitivity of the overall instrument when the greatest proportion of light is scattered in the forward direction at small angles.

One method for detecting the light scattered at small angles to the axis of said light beam provides for the positioning of a very large detector cell at one end of the receiving zone such as a disc with a relatively small central hole to permit the passage of said unscattered light beam. This method is appropriate for low sensitivity applications such as domestic installations.

For commercial/industrial applications such cells are not usually available with sufficient sensitivity and low noise, so for a detector of sufficient sensitivity a comparatively small cell must be used. To capture and focus sufficient scattered light onto said small cell, a concave mirror or lens could be used. However, optical loss and alignment criticality must be minimized so a concave mirror employing only one reflection is preferred, furthermore it enables the wavelength of light to be altered such as from visible light to infra-red light without altering focussing requirements.

Thus, there is also provided according to the present invention a light sensing device for use in a fluid pollution monitoring apparatus, including a fluid sampling chamber, means for providing or projecting a coherent collimated light beam into said sampling area, aspirator means introducing sample fluid from an area to be monitored into said sampling area to be exposed to said light beam, a light detector cell positioned at a location separated or shaded from said light beam, reflecting means in said sampling area focussing as much as possible of the available scattered light towards said reflecting means onto said detector cell. Preferably said reflecting means is an axially disposed concave reflector.

In a preferred form of the invention at least two reflective segments are provided to reflect differing proportions of light scattered either at small angles or angles up to 90° to the light beam towards at least two detector cells receiving that differing proportion of light respectively in response to incidence of particles of differing size.

This invention provides an opportunity for substantial improvement in the ratio of scattered light to remnant incident light, improving the "optical signal-to-noise ratio". According to this invention, the incident light intensity (required to produce a given scattered light intensity appropriately matched to the sensitivity of said detector cell), may be reduced. Therefore the energy consumption of the light source may be reduced. Use of a Xenon lamp in the prior an accounted for the majority of the power consumption of the entire instrument, Thus it is possible in the present invention to provide for a substantial reduction in power consumption. Moreover there is provided an opportunity for increased sensitivity of the overall instrument, such that lower levels of particle concentration can be detected.

In order to improve the electrical signal-to-noise ratio of the detector cell, the laser beam may be pulsed or modulated. The modulation frequency may be synchronised with a digital filter means provided by a phase-locked loop or microprocessor circuit (not shown), to optimise the signal-to-noise ratio. This modification further reduces the required intensity of the laser beam, reducing the energy consumption of the overall instrument. If the laser lamp is pulsed (at say 100 Hz), maximum opportunity for reduced energy consumption and increased operational life may be achieved).

A feature of the present invention is the ability to position the sampling chamber closely adjacent to the aspirator means enabling the positioning of a relatively narrow throat in the sampling chamber adjacent to the aspirator diffuser, and enabling an integral construction of aspirator and sampling chamber thereby minimizing loss of pressure from the aspirator.

In taking advantage of the reducing cost and improving availability of miniature lasers such as solid state or Helium-Neon lasers in the performance of the present invention, either type may be used however, the more expensive visible lasers, having a shorter wavelength, would provide greater sensitivity.

In one form of the invention a further reflecting means is placed at the centre, and in front of said reflecting means, to reflect said light beam in a desired direction, such as back towards said source or towards a light absorbing means within or beyond said sampling area.

Said detector cell is mounted at the rear of said further reflecting means, and positioned to receive scattered light which has been collected and focussed by said concave reflector. Thus the detector cell is prevented from detecting direct light from said laser beam but will receive a large proportion of the scattered light which is received by said further reflecting means.

This arrangement does not require a reflective wall chamber, and does not require a chamber of special shape such as an elliptical shape. Therefore, it will be appreciated that any dust build-up on chamber walls would not necessarily affect the sensitivity of the monitor apparatus. By suitable deflection of the air stream and with careful attention to chamber orientation or air turbulence and velocity the concave reflector can be made practically resistant to dust build-up.

A combination of a reflective elliptical wall chamber and concave reflector to achieve a resultant combination of all sources of reflected light is also possible according to the present invention.

When using the instrument to detect very small particles or molecules, or for the purposes of calibration, because the narrow optical bandwidth of a laser may bias the detector sensitivity in favour of certain particle sizes (thus rendering comparatively lower sensitivity to other size particles); conveniently two collinear laser beams operating at different wavelengths may be provided.

Figure 1:
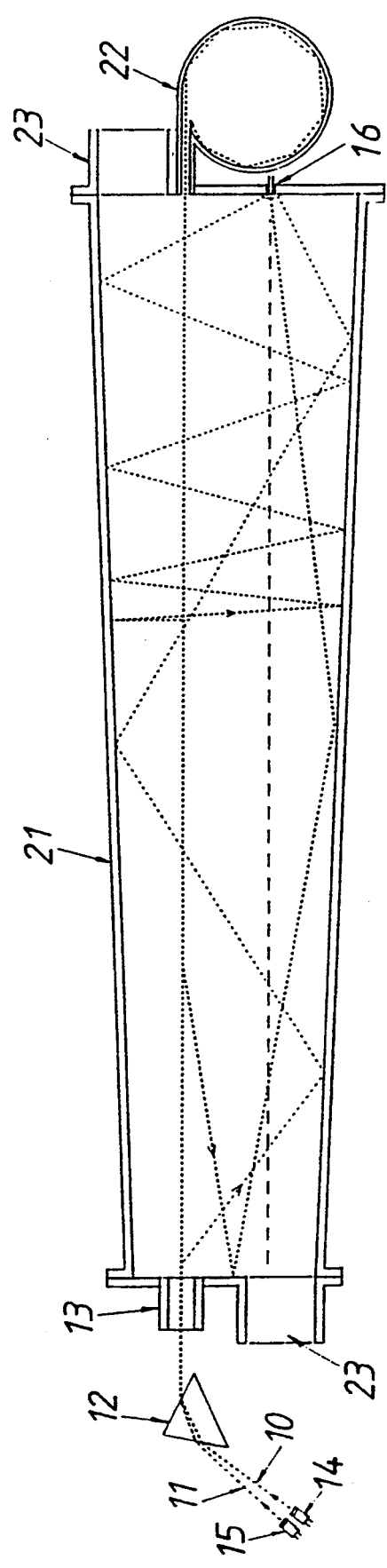
FIG. 1 shows a sectional view of a sampling chamber for a light sensing pollution detection device.
Figure 2:
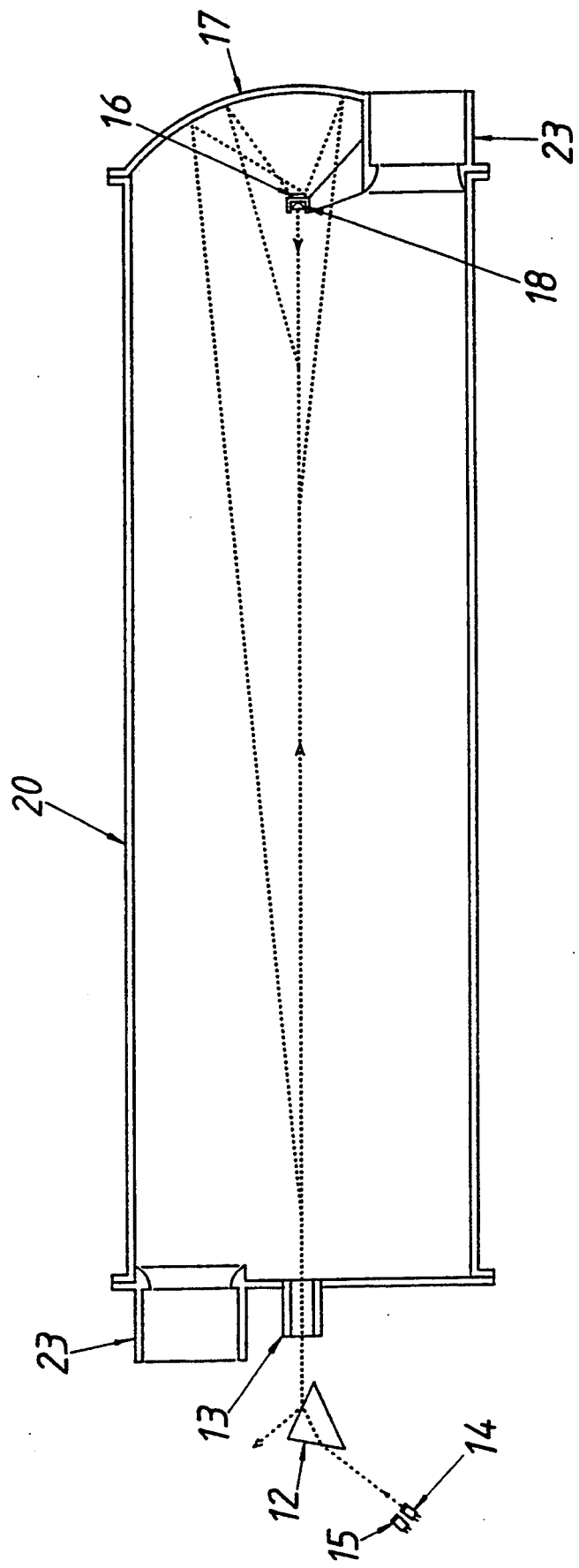
FIG. 2 shows a further embodiment of a sampling chamber.

In one embodiment of the invention as illustrated in FIGS. 1 and 2, the two laser beams may be rendered collinear by use of a prism 12 or mirror system. One embodiment of such a system would utilize the differing angle of refraction applicable to each wavelength. By use of a single prism 12, each laser beam would be projected at a differing incident angle such that the two beams emerge as a pair of collinear beams into the collimator 13. This novel employment of differing angle of incidence allows for the necessary physical separation of the two lasers 14, 15. It would be possible to operate both laser beams at the same time, and/or to alternate each beam to provide additional information about the nature of the particles or fluid.

If the laser beams are directed back towards said source, they strike said prism at a preset angle and may be reflected toward a light absorbing means. Alternatively, a light absorbing means may be employed within or without the chamber and thus allow less critical alignment of said reflecting means.

Naturally the said detector cell 16 must be responsive to both laser wavelengths. If said detector cell has differing sensitivity at the two said laser wavelengths, each said laser could be pulsed alternately at a rate synchronised with a switched-gain amplifier means to compensate for said differing sensitivity. It is know that the light-scattering coefficient for any gas or aerosol is dependent upon the wavelength of the incident light. Rayleigh has found that for gases, this coefficient varies inversely with the fourth power of the wavelength employed. Larger airborne particles have a coefficient which varies inversely with an exponent less than four (possibly as low as zero). Therefore, for a given span of airborne particle sizes, said compensation means could also be used to compensate for the differing light-scattering coefficients at the two said laser wavelengths. Alternatively the whole instrument could be used to determine the said exponent for a known air/gas/particulate sample.

With specific reference to FIG. 1, a novel circular light absorbing device 22 is shown for receiving the unscattered light beam travelling through the chamber. The device is circular as shown with glossy reflective walls so that received light is continually reflected at reducing intensity around the walls as shown and prevented from returning into the sampling chamber. Similar results are of course achievable with other configurations such as for example elliptical walls.

In an alternative arrangment the chamber is in the form of a highly reflective elliptical tube. The light beam is projected along one focus of the elliptical tube. Particles present in the path of the light beam cause scattering in all directions but the elliptical chamber causes much of the scattered light to pass through the second focus of the elliptical tube after one reflection and again after multiple reflections. It is to be noted that in the instance of multiple reflections the light rays will be constrained to align with the two focal points.

Scattered light is received by reflector 17 (FIG. 2) for focussing the large proportion of scattered light onto the detector cell 16. The cell preferably has a finite dimension to enable receipt of more light without the necessity to focus the light to a sharp point. A lens or lens system (not shown) may be used as an alternative to the reflector, however a compound lens would be required if focussing is to be achieved at more than one wavelength.

It is possible to achieve adequate sensitivity for some applications by utilizing a light emitting diode (LED) as an alternative to a double or single laser beam. Port means 23 are provided for introducing sample air into and out of the chamber.

With reference to FIGS. 3 to 6 there is described further embodiments of the invention including a sample tube 30 containing a flowing sample of air is connected to an aspirator 31 for drawing air in from an area such as a room or like being monitored for smoke or dust or like pollution.

A laser beam is generated and projected into tube 32 to traverse the sample tube 30 and is projected into a light receiving zone 33 through a cone shaped aperture 35. As previously described, light impinging upon dust or smoke particles in the air stream is scattered at angles into the light receiving zone whilst unscattered light follows a narrow path directly into a light receiving absorbing area 34. The scattered light pattern is configured as a conical section to confine scattered light into the conical shaped receiving area as shown in dotted outline 36 in FIG. 5 and 6.

The conical receiving zone includes a reflective wall 37 for reflecting scattered light into the zone 36 onto a detector cell 38 which is well away from any possibility of direct contact with the unscattered light component.

The air sampling tube 30 is narrowed to form a nozzle to reduce the cross-sectional area 30(a) and this point is selected to project the light beam through the air stream. Thus the air stream is fast moving and the area of light relative to the cross-sectional area of the sample area is relatively high, thereby ensuring a high incidence of detection of particles in the sample area. That is, a relatively small area of the sample tube and the sampling area is unaffected by the traversing light beam.

The light receiving zone preferably has an included angle $\phi$ of not more than 50° and it is the scattered light within this relatively narrow zone that is reflected and focused by reflector 37 onto the detector 38.

Thus the cell sensitivity is maintained with at least 90% of normal signal strength by ensuring an included angle of received light at the detector 38 of not more than 50°.

The diameter of the laser beam exit aperture 39 in the reflector 37 is in the range of 3–5 mm corresponding to a small scatter angle of less than 5°, thereby avoiding detection of particles which fall outside the maximum size particles that occur in smoke. Thus it is possible for the detector to be constructed to discriminate between detection of particles of large size or alternatively a detector may be constructed which is sensitive to both ranges of particle size and embodying a segmented reflector with reflector surfaces of differing focal position operating in conjunction with at least a pair of detector cells that are activated by the existence of smaller smoke particles on the one hand or larger dust particles on the other hand.

Figure 6:
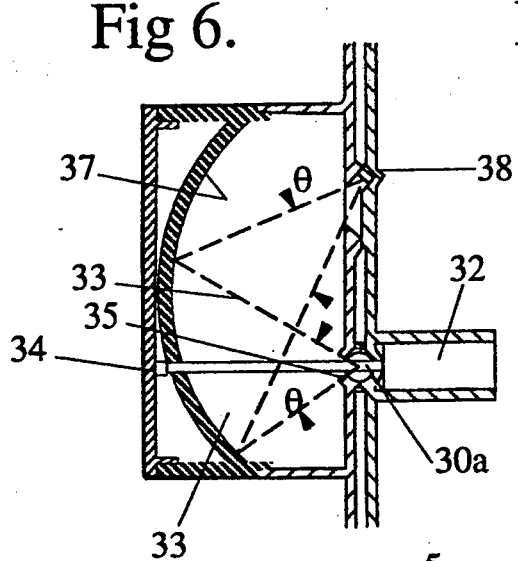
FIG. 6 is a sectional view of the sampling device taken on line 6—6 of FIG. 4.
Figure 5:
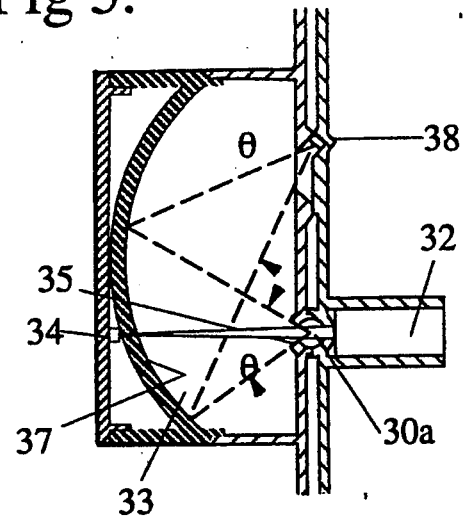
FIG. 5 is a sectional view of the sampling device taken on line 5—5 of FIG. 3.
Figure 3:
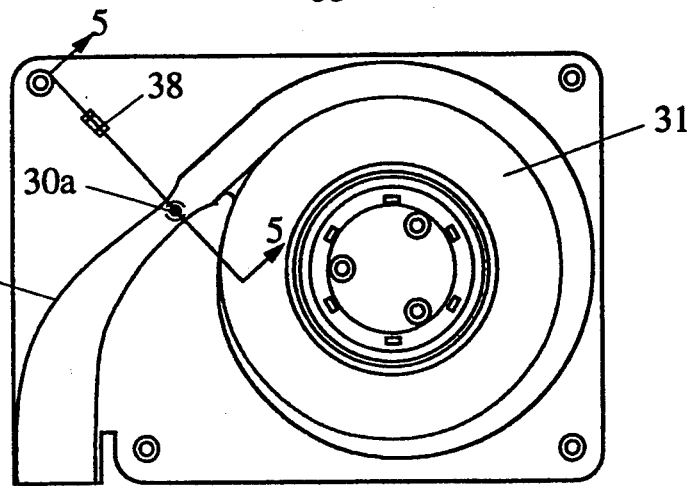
FIG. 3 shows a further embodiment of a sampling device.
Figure 4:
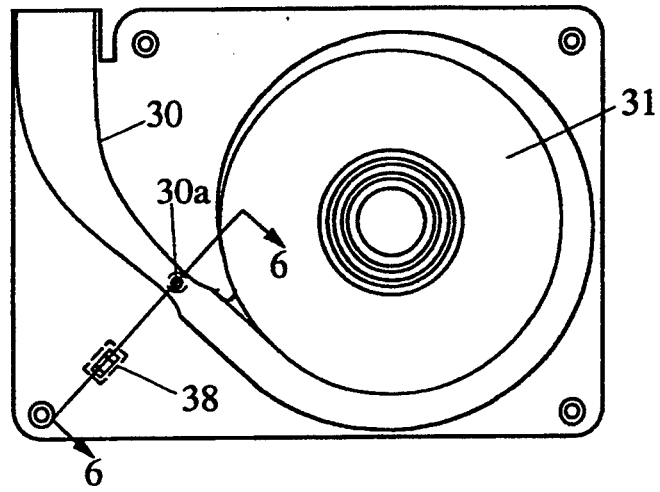
FIG. 4 shows a further embodiment of a sampling device.
Figure 10:
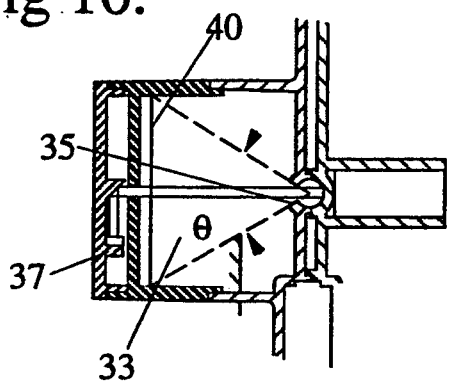
FIG. 10 is a section view taken on line 10—10 of FIG. 8.
Figure 9:
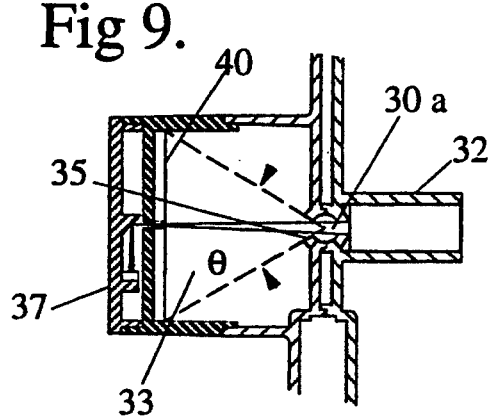
FIG. 9 is a sectional view taken on line 9—9 of FIG. 7.
Figure 7:
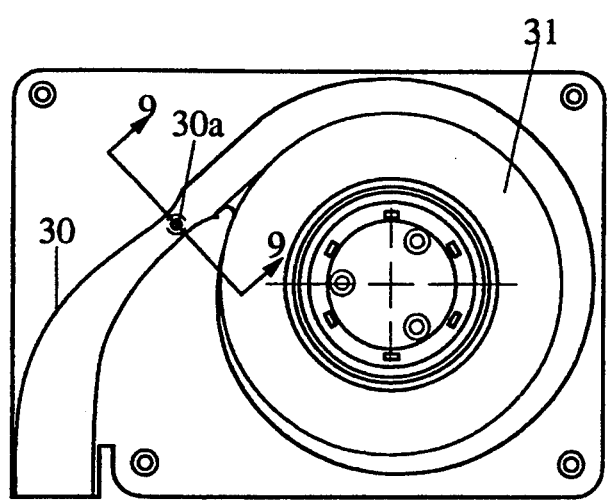
FIG. 7 shows a further embodiment of a sampling device.
Figure 8:
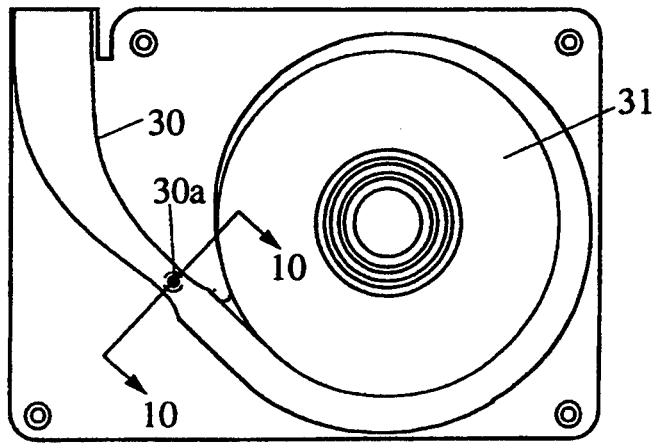
FIG. 8 shows a further embodiment of a sampling device.

A further embodiment is illustrated in FIGS. 7–10, which is useful for lower sensitivity applications wherein a polycrystalline solar cell 40 is provided having a relatively large area/low cost but adequate sensitivity for some applications such as residential areas. In this arrangement scattered light from impinged particles in the sample area tube 30(a) is received in the receiving zone 33 forming a similar cone angle $\phi$ that is shown in FIGS. 5 and 6 which should not exceed 50° and is adapted to activate an alarm circuit upon receipt of impinging light. The receiving surface 37 is apertured at the central axis 39 to receive and absorb the unscattered laser beam.

We claim:

1. A fluid pollution monitoring apparatus including a fluid sampling means, means for projecting a coherent collimated light beam into said sampling means, means introducing sample air from an area to be monitored into said sample means to be exposed to said light beam, such that any particles present in said sample act to scatter said light beam into a scattered light receiving zone, a light detector cell positioned at a location within the scattered light receiving zone, means for directing scattered light produced by the presence of airborne particles towards said detector, the scattered light pattern being of substantially cone shape in cross-section taken on a plane along the axis of coherent collimated light beam such that said scattered light receiving zone is formed by a conical area having an included angle not exceeding 50°.

2. A fluid pollution monitoring apparatus including a fluid sampling means, a light emitting diode for projecting a high intensity light beam into said sampling means, aspirator means introducing sample air from an area to be monitored into said sample means to be exposed to said light beam into a scattered light receiving zone, a light detector cell positioned in the scattered light receiving zone, means for directing any scattered light produced by the presence of airborn, particles towards said detector, the scattered light pattern being of substantially cone shape in cross-section taken on a plane of the axis of said light beam.

3. A monitoring apparatus as claimed in claim 1 or 2 wherein the detector cell has a relatively large area located at one end of said receiving zone and formed as a disc with a relatively small central aperture adapted to permit the passage of unscattered light beam therethrough and ensuring that unscattered light does not impinge upon said detector disc.

4. A monitoring apparatus as claimed in claim 3 wherein said central aperture has a dimension in the range of 3 to 5 mm corresponding to a small scatter angle of less than 5° in the light receiving zone to thereby avoid detection of particles which are larger than the maximum size of smoke particles.

5. A fluid pollution monitoring apparatus as claimed in claims 1 or 2, wherein said light beam is generated by at least two laser beams operating at different wavelengths adapted to be projected through a single prism into said sampling chamber as a pair of co-linear beams.

6. A fluid pollution monitoring apparatus as claimed in claim 5, wherein the output of said light detector means varies in proportion to the level of scattered light received to provide a measure of the concentration of particles and therefore fluid pollution within said chamber.

7. A fluid pollution monitoring apparatus as claimed in claim 6, wherein said detector means comprises an optical fibre or lasing rod means, a detector cell located at or near one end of said optical fibre or lasing rod means to receive scattered light directed along the length of said optical fibre or lasing rod means.

8. A fluid pollution monitoring apparatus as claimed in claim 1, wherein said light beam is generated by a high intensity light emitting diode directing its light into a collimator.

9. A fluid pollution monitoring apparatus as claimed in claim 1 wherein said means for introducing sample air includes an aspirator closely adjacent to said sampling means, said sampling means including a nozzle portion at the outlet of said aspirator to form a sampling area of reduced cross-sectional area the cross-sectional area of the light beam projected through the sampling area relative to the sampling area being relatively high thereby ensuring a high incident of detection of any particles occurring in the sample area, whilst minimzing loss of pressure from the aspirator.

10. A monitoring apparatus as claimed in claim 1 or 2 wherein said means for directing scattered light includes a segmented reflector means with reflector surfaces of differing focussing position at which at least a pair of detectors are positioned, such that scattered light generated by the existence of small particles on the one hand or large particles present in the sampled air on the other is detected by at least one of said pair of detectors, each located at a differing focussing position of the segmeted reflector means.

11. A fluid pollution monitoring apparatus as claimed in claim 2 wherein the unscattered light beam is absorbed by a light receiver having a substantially cylindrical reflective interior wall.

12. A fluid pollutioon monitoring apparatus as claimed in claim 11 wherein unscattered light is turned through substantially 90° to impinge upon said reflective interior wall.

* * * * *

UNITED STATES PATENT AND TRADEMARK OFFICE
CERTIFICATE OF CORRECTION

PATENT NO. : 5,392,114
DATED : February 21, 1995
INVENTOR(S) : Martin T. Cole

It is certified that error appears in the above-indentified patent and that said Letters Patent is hereby corrected as shown below:

Column 4, line 51, change "an" to -- art --; line 53, change "," to -- . --.

Column 9, line 8, change "minimzing" to -- minimizing --.

Signed and Sealed this

Sixteenth Day of May, 1995

Attest:

BRUCE LEHMAN

Attesting Officer     Commissioner of Patents and Trademarks